United States Patent [19]

Kato et al.

[11] 4,093,630

[45] June 6, 1978

[54] DIAZABICYCLOALKANE DERIVATIVES

[75] Inventors: Hideo Kato, Katsuyama; Tomoyasu Nishikawa, Ono; Eiichi Koshinaka, Katsuyama, all of Japan

[73] Assignee: Hokuriku Pharmaceutical Co., Ltd., Fukui, Japan

[21] Appl. No.: 804,591

[22] Filed: Jun. 8, 1977

[30] Foreign Application Priority Data

Jun. 10, 1976  Japan .................................. 51-67158

[51] Int. Cl.² .......................................... C07D 487/08
[52] U.S. Cl. ..................... 260/326.85; 260/239.3 B; 260/326.62; 424/274
[58] Field of Search ..................................... 260/326.85

[56] References Cited

U.S. PATENT DOCUMENTS

| | | | |
|---|---|---|---|
| 2,655,498 | 10/1953 | Weston et al. | 260/239 BC |
| 2,891,060 | 6/1959 | Rudner | 260/326.85 |
| 3,732,212 | 5/1973 | Carabateas | 260/326.85 |

*Primary Examiner*—Alton D. Rollins
*Attorney, Agent, or Firm*—Burgess, Ryan and Wayne

[57] ABSTRACT

Novel diazabicycloalkane derivatives of the formula

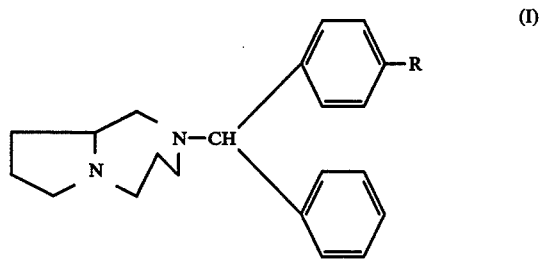

wherein R is hydrogen or a halogen including acid addition salts thereof are provided including a process for their preparation. These compounds are useful as antihistamines.

5 Claims, No Drawings

DIAZABICYCLOALKANE DERIVATIVES

The present invention relates to a novel diazabicycloalkane derivative and a process of producing the same. More particularly, the present invention relates to a novel pyrrolo[1,2-a][1,4] diazepine derivative which is useful as an antihistamic agent, and a process for producing the same.

The diazabicycloalkane derivative in accordance with the present invention is represented by the formula I:

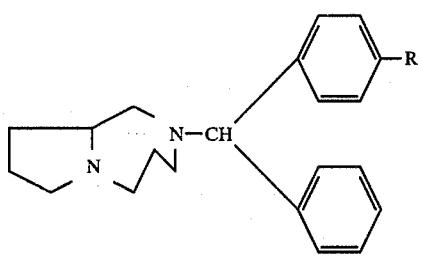

wherein R represents a hydrogen atom or a halogen atom.

Examples of the halogen atoms in the formula above are chlorine, bromine, iodine, etc.

The diazabicycloalkane derivative of the present invention, represented by the formula I, is prepared by reacting pyrrolo [1,2-a] [1,4] diazepine represented by the formula II:

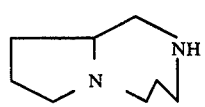

with a benzhydryl halide derivative represented by the formula III:

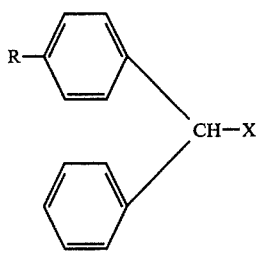

wherein R has the same meaning as defined above and X represents a halogen atom.

It is advantageous to carry out the reaction in a solvent. Any solvents are usable as far as they do not prevent the reaction. Typical examples of these solvents include benzene, toluene, xylene, methanol, ethanol, isopropanol, n-butanol, dimethylformaide, dimethylsulfoxide, etc. The reaction advantageously proceeds in the presence of an acid acceptor such as a tertiary amine, sodium carbonate, potassium carbonate, sodium alkolate, sodium hydride, sodium amide, sodium iodide, etc. If an excess amount of the compound represented by the formula II is used, the compound can be the acid acceptor.

The reaction temperature should preferably be at about boiling point of the solvent used.

Pyrrolo [1,2-a][1,4] diazepine represented by the formula II is synthesized in accordance with the following method. The products are both optically active since L-proline is used herein as a starting material.

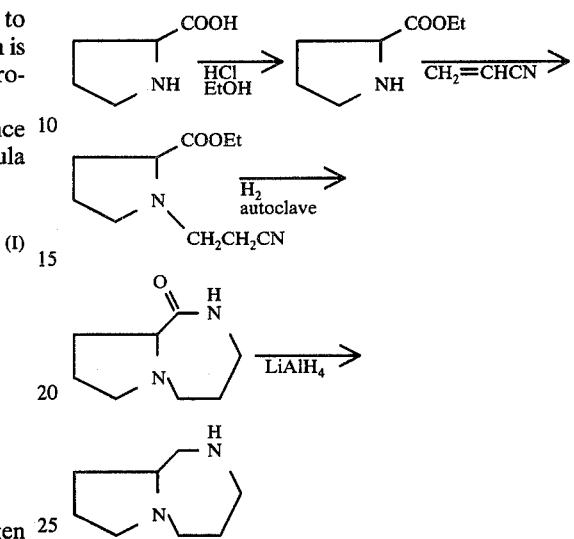

The compound represented by the formula I may be converted to acid addition salts thereof, e.g., hydrochloride, hydrobromide, sulfate, oxalate, maleate, citrate, fumarate, etc.

The compound represented by the formula I is useful as an antihistamic agent. The compound is administered orally in the form of a capsule or tablet or parenterally, with a pharmaceutically acceptable carrier, in an effective amount usually varying between about 5 to about 100 mgs.

Comparison of the compound represented by the formula I with a known compound has been made with respect to antihistamic activity, the results of which are as follows.

EVALUATION OF ANTIHISTAMIC ACTIVITY

Antihistamic effect was examined in accordance with the Magnus method, using the ileum extracted from a mongrel dog. The effect was evaluated by determining the $PA_2$ value by the Takayanagi method. Comparison with a known compound is shown in the table below.
Known Compound:
Diphenhydramine hydrochloride Compounds of Invention:
  I: 2-Benzhydryloctahydro-1H-pyrrolo[1,2-a][1,4]diazepine dihydrochloride (Compound of Example 1)
  II: 2-(p-Chlorobenzhydryl) octahydro-1H-pyrrolo[1,2-a][1,4]diazepine (Compound of Example 2)

Table

| Compound | $PA_2$ |
|---|---|
| Diphenhydramine hydrochloride | 8.15 + 0.04 |
| Compound I | 8.25 + 0.05 |
| Compound II | 8.42 + 0.12 |

As can be seen from the results above, the compounds of the present invention are sufficiently comparable with the known compound and even better.

The present invention will be explained in more detail with reference to the examples herebelow.

EXAMPLE 1

2-Benzhydryloctahydro-1H-pyrrolo[1,2-a][1,4]diazepine dihydrochloride

A mixture of 2.8 g. of octahydro-1H-pyrrolo[1,2-a][1,4]diazepine, 4.9 g. of benzhydryl bromide and 4.1 g. of anhydrous potassium carbonate in 40 ml. of distilled benzene was stirred for 16 hrs. under reflux. The reaction mixture was washed with 50 ml. of a 5% potassium carbonate solution and the benzene layer was dehydrated. After evaporating the solvent off, the residue was converted to the dihydrochloride in a conventional manner. After recrystallizing from isopropanol, the product having a melting point of 183°–185° C. was obtained (yield 4.8 g.; $[\alpha]_D = -15.9°$ (C=1, water)).

| Elemental Analysis: $C_{21}H_{26}N_2 \cdot 2HCl$ | | |
|---|---|---|
| Calcd. C: 80.78 | H: 7.44 | N: 7.38 |
| Found C: 80.72 | H: 7.48 | N: 7.33 |

EXAMPLE 2

2-(p-Chlorobenzhydryl) octahydro-1H-pyrrolo[1,2-a][1,4]diazepine:

The same procedures as in Example 1 were repeated except that 2.1 g. of octahydro-1H-pyrrolo[1,2-a][1,4]diazepine, 4.2 g. of p-chlorobenzhydryl bromide and 3.0 g. of anhydrous potassium carbonate were employed. The product having a boiling point of 190°–191° C./1.5 mmHg was thus obtained in an amount of 3.6 g. $[\alpha]_D = -16.7°$ (C=1, chloroform).

What is claimed is:

1. A diazabicycloalkane compound of the formula:

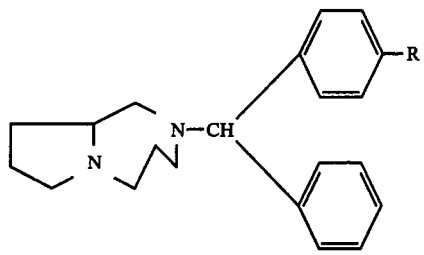

wherein R represents a hydrogen atom or a halogen atom selected from the group consisting of chlorine, bromine and iodine, and therapeutically acceptable acid addition salts thereof.

2. A compound as claimed in claim 1 wherein R is a hydrogen atom, and the therapeutically acceptable acid addition salts thereof.

3. A compound as claimed in claim 1 wherein R is a chlorine atom and the therapeutically acceptable acid addition salts thereof.

4. 2-benzhydryloctahydro-1H-pyrrolo[1,4]diazepine dihydrochloride.

5. 2-(p-chlorobenzhydryl) octahydro-1H-pyrrolo[1,2-a][1,4]-diazepine.

* * * * *